United States Patent
Li et al.

(10) Patent No.: US 7,332,617 B2
(45) Date of Patent: Feb. 19, 2008

(54) PROCESS FOR THE PREPARATION OF DOCETAXEL TRIHYDRATE

(75) Inventors: Jinliang Li, Shanghai (CN); Zuwang Wu, Shanghai (CN)

(73) Assignees: Shanghai Desano Chemical Pharmaceutical Co., Ltd., Shanghai (CN); Shanghai Desano Pharmaceuticals Science & Technology Development Co., Ltd., Shanghai (CN)

( * ) Notice: Subject to any disclaimer, the term of this patent is extended or adjusted under 35 U.S.C. 154(b) by 246 days.

(21) Appl. No.: 10/555,889

(22) PCT Filed: Apr. 13, 2004

(86) PCT No.: PCT/CN2004/000343

§ 371 (c)(1),
(2), (4) Date: Nov. 7, 2005

(87) PCT Pub. No.: WO2004/099167

PCT Pub. Date: Nov. 18, 2004

(65) Prior Publication Data

US 2006/0217436 A1    Sep. 28, 2006

(30) Foreign Application Priority Data

May 8, 2003   (CN)   ................. 03 1 16815

(51) Int. Cl.
*C07D 305/14*    (2006.01)
(52) U.S. Cl. .................................................. 549/510
(58) Field of Classification Search ................ 549/510
See application file for complete search history.

(56) References Cited

U.S. PATENT DOCUMENTS

| 4,814,470 | A | 3/1989 | Colin et al. |
| 5,688,977 | A | 11/1997 | Sisti et al. |
| 6,022,985 | A | 2/2000 | Authelin et al. |
| 6,107,497 | A | 8/2000 | Sisti et al. |
| 2003/0158249 | A1 | 8/2003 | Chi et al. |

OTHER PUBLICATIONS

Milanesio, M., et al., "Ab Initio Conformational Study of the Phenylisoserine Side Chain of Paclitaxel," Med. Chem. 42:291-299 (1999).
Zaske, L., et al., "Docetaxel: Solid State Characterization by X-Ray Powder Diffraction and Thermogravimetry," J. Phys. IV France 11(Pr10):221-226 (2001).

*Primary Examiner*—Taofiq Solola
(74) *Attorney, Agent, or Firm*—Perkins Coie LLP; Manni Li

(57) ABSTRACT

A method to prepare Docetaxel trihydrate using the mixture of acetone and water, which provides the product with good stability, less experiment time, less exposal to light, and avoids purity decreasing. The process is simple and easy to operate.

9 Claims, No Drawings

PROCESS FOR THE PREPARATION OF DOCETAXEL TRIHYDRATE

FIELD OF THE INVENTION

This invention is under the field of medicine synthesization technique, involving the method to prepare the compound of Docetaxel trihydrate.

BACKGROUND OF THE INVENTION

The formal name of Docetaxel trihydrate is (2'R,3'S)-N-carboxy-3-phenylisoserine, N-tert-butyl ester, 13-ester with 5β,20-epoxy-1β,2α,4α,7β,10β,13α-hexahydroxytax-11-en-9-one 4-acetate-2-benzoate, trihydrate.

Docetaxel is a kind of new anti-cancer medicine that is being developed abroad in recent years. Being the representative of the 2nd generation of taxane medicine family, Docetaxel attracts more and more attention from people for its enhanced water-solubility and wide spectrum of excellent anti-cancer characteristic. Docetaxel has activity against several kinds of cancer, including breast cancer, non small cell lung cancer and other malignant tumours (prostate cancer, esophagus cancer and malignant tumour in head or neck, etc.), which is one of the most effective single medicine for treating the transferring breast cancer. The especially remarkable result of it is: in phase II clinical trial, for those patients who have received any chemotherapy (including those patient with primary resistence against anthracene, the total chemotherapy efficiency of single Docetaxel was 47% (generally 100 mgs/m$^2$, infusion, once per 3 weeks). A few research reports showed that the efficiency of this drug is between 32% and 58%, among which one research reported CR (Complete Resultful) at 4%. For patients in the later-stage of none small cell lung cancer, no matter he/she was in the beginning of treatment, or has passed the progress of cis-platinum chemotherapy, the medicine proved its special anti-cancer activity.

Docetaxel can promote microtubule proteins to be assembled into microtubule and inhibit its disassembled. Docetaxel also has the good bioavailability, higher intracellular concentration and longer intracellular retention-time.

Docetaxel is the first semi-synthesized taxus medicine. It has been launched in the markets of Europe/America countries.

According to Chinese patent 95193984.X, Docetaxel trihydrate is more stable than its anhydrous compound. So we decided to add a crystallization process into the production procedure of the drug production. Ethanol and water are selected as solvents. But in this experiment process, the inventor discovered that use of the ethanol produces not only more time expense for concentration and higher water bath temperature, but also smaller crystal grain, thus longer time to filter and collect products is needed.

SUMMARY OF THE INVENTION

The present invention provides a method to prepare Docetaxel trihydrate having the following steps. Under temperature of 10-39° C., put anhydrous Docetaxel (purity of HPLC>99.5%) in 8~12 parts acetone to fully dissolve. Then under the same temperature, and reduced pressure concentrate it to form oil-like matter, add certain quantity of acetone to fully dissolve, concentrate in reduced pressure again to form oil-like matter, then add certain quantity of acetone to fully dissolve, add dropwise certain quantity of purified water, the procedure will last 10~60 min. Control the dropping speed to avoid the growth of agglomeration during the process. Then cool the product under 0° C. for 2-5 hours, filter by suction, then wash the residue cake with the mixture of acetone and water (1:1~1:5), dry on $P_2O_5$ in vacuum till the weight is constant, the product obtained is Docetaxel trihydrate.

DETAILED DESCRIPTION OF THE INVENTION

This invention is to overcome the shortcoming of the above method and to design an improved one. This invention offers a method to prepare Docetaxel trihydrate: Under temperature of 10-39° C., put anhydrous Docetaxel (purity of HPLC>99.5%) into 8~12 parts (by weight) of acetone to be fully dissolved. Then at the same temperature, under reduced pressure concentrate it to form oil-like matter, add certain quantity of acetone to fully dissolve it, and concentrate it again to form oil-like matter, then add certain quantity of acetone to fully dissolve it, add dropwise certain quantity of purified water, the procedure will last 10~60 min. Control the dropping speed to avoid the growth of agglomeration during the process. Then cool the product under 0° C. for 2-5 hours, make suction filtration, then wash the residue cake with the mixture of acetone and water (1:1~1:5), dry it on $P_2O_5$ in vacuums till the weight is constant. The product is Docetaxel trihydrate.

The invention uses acetone and water to prepare Docetaxel trihydrate, which has the following advantages:

1. Less operation time. Because the crystal granule from acetone and water is big, and this has shorten the filtration time. The crystal granule from ethanol and water is smaller, so the filtration time is 3 hours; while the time is 1 hour for acetone and water.

It is found during the experiment that Docetaxel's purity dropped when it was exposed in light for 10 hours. It is sensitive to light in some way. Shortening of the filtration time decreased the exposure time, thus the reduction of purity was avoided.

2. Lower operation temperature (below 40° C.). As Docetaxel's stability is bad in high temperature, this will help to avoid any purity drop of Docetaxel in purification process.

A patent document mentions that the reaction temperature is 40~60° C. if ethanol is used. But if acetone is used, the reaction may found ≦39° C. Lower temperature makes the experiment easier for operation.

The product from the invention process was proved to be compound trihydrate by methods of thermogravimetric analysis and thermo-differential analysis. Under the temperature of 55~115° C., the mass loss was 6.8%, which is in accordance with the 3 crystallized water in the compound.

Product from this method was proved to have the same good stability as that stated in the patent document. The experiment conditions for testing the stability are: under temperature of 40° C., at relative humidity of 75%, 12 months. Within this period, the trihydrate compound remain no change.

The embodiments illustrated and discussed in this specification are intended only to teach those skilled in the art the best way known to the inventors to make and use the invention. Nothing in this specification should be considered as limiting the scope of the present invention. All examples presented are representative and non-limiting.

The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

EXAMPLE 1

Under 20° C., put 87 g anhydrous Docetaxel (purity of HPLC>99.5%) into 1044 ml acetone to fully dissolve, then at 40° C. under reduced pressure concentrate it to form oil-like matter. Add 348 ml acetone to dissolve the oil-like matter, and again concentrated it to form oil-like matter. Add 1740 ml acetone to dissolve it well, then keep the temperature at 15° C. and drop 2610 ml purified water slowly, which lasts 15 min. The dropping speed should be controlled to avoid agglomeration. After that, cool it under 0° C. for 2 hours and then make suction filtration. Then wash the residue 3 times with 200 ml mixture of acetone and water (1:1.5). Dry it on $P_2O_5$ in vacuums for 5 hours till it obtains a constant weight. The trihydrate compound is 85 g with 6.43% of water content.

EXAMPLE 2

Under 40° C., put 200 g anhydrous Docetaxel (purity of HPLC>99.5%) into 2850 ml acetone to fully dissolve, then at 40° C., under reduced pressure concentrate it to form oil-like matter. Add 950 ml acetone to dissolve the oil-like matter, and again concentrated it to form oil-like matter, add 4750 ml acetone to dissolve it well, then keep the temperature at 15° C. and drop 9975 ml purified water slowly, which lasts 50 min. The dropping speed should be controlled to avoid agglomeration. After that, cool it under 0° C. for 4 hours and then make suction filtration. Then wash the residue 3 times with the 580 ml mixture of acetone and water (1:3.5). Dry it on $P_2O_5$ in vacuums for 6.5 hours till it obtains a constant weight. The compound is 196.5 g with 6.2% of water content.

We claim:

1. A method for preparing Docetaxel trihydrate, comprising:

dissolving anhydrous Docetaxel in acetone at a ratio of about 1:(8-12) by weight to form a mixture, concentrating the mixture to form an oil-like matter and re-dissolving the oil-like matter in acetone to obtain a solution, adding dropwise purified water to the solution while controlling drop speed to avoid growth of agglomeration, and cooling the solution to obtain crystalline Docetaxel trihydrate.

2. The method according to claim 1, wherein the anhydrous Docetaxel is dissolved in acetone at about 10-39°C.

3. The method according to claim 1, wherein the anhydrous Docetaxel has a purifty of HPLC>99.5%.

4. The method according to claim 1, wherein the concentration of the solution of Docetaxel to form the oil-like matter is repeated, and the oil-like matter is dissolved in acetone to form a solution.

5. The method according to claim 1, wherein a duration for adding purified water dropwise lasts about 10-60 minutes.

6. The method according to claim 1, wherein the solution is cooled at 0°C. for about 2-5 hours.

7. The method according to claim 6, further comprising suction-filtering the solution to obtain a residue cake, washing the residue cake in a mixture of acetone and water, and drying the washed residue cake to obtain the Docetaxel trihydrate.

8. The method according to claim 7, wherein the residue cake is washed in the mixture of acetone and water at a ratio of about 1: (1-5).

9. The method according to claim 7, wherein the washed residue cake is dried on $P_2O_5$ in vaccum until weight of the residue cake is constant.

* * * * *